United States Patent

Frey et al.

[11] Patent Number: 5,176,708
[45] Date of Patent: Jan. 5, 1993

[54] PROSTHETIC IMPLANT

[75] Inventors: Otto Frey, Winterthur; Peter Dittes, Oberdurnten; Rudolf Koch, Berlingen, all of Switzerland

[73] Assignee: Sulzer Brothers Limited, Winterthur, Switzerland

[21] Appl. No.: 662,195

[22] Filed: Feb. 28, 1991

[30] Foreign Application Priority Data

Mar. 12, 1990 [CH] Switzerland ............ 00787/90

[51] Int. Cl.⁵ .............................................. A61F 2/08
[52] U.S. Cl. ..................................................... 623/13
[58] Field of Search ................................... 623/13, 14

[56] References Cited

U.S. PATENT DOCUMENTS

| | | | |
|---|---|---|---|
| 3,540,452 | 11/1970 | Usher et al. ............ | 28/335.5 |
| 4,246,660 | 1/1981 | Wevers ..................... | 606/71 |
| 4,345,339 | 8/1982 | Müller et al. ............. | 623/13 |
| 4,728,329 | 3/1988 | Mansat ..................... | 623/13 |

FOREIGN PATENT DOCUMENTS

| | | | |
|---|---|---|---|
| 708000 | 4/1965 | Canada ..................... | 623/13 |
| 0238263 | 9/1987 | European Pat. Off. . | |

*Primary Examiner*—Randy C. Shay
*Attorney, Agent, or Firm*—Kenyon & Kenyon

[57] ABSTRACT

The ligament prosthesis is formed of concentric tubes of filaments threads. In addition, a layer of elastomer is disposed over at least the outermost tube to act as an impermeable layer to the passage of abraded material from within the tubes into the lining. The thickness of the elastomer layer is at most 0.1 millimeter. The elastomer may also be provided on and about the threads of the inner tubes to reduce a migration of abraded particles therein.

2 Claims, 2 Drawing Sheets

PROSTHETIC IMPLANT

This invention relates to a prosthetic implant. More particularly, this invention relates to a prosthetic implant which can be used as a ligament prosthesis.

Heretofore, various types of prosthetic implants have been known for implanting in a human body, for example for use as a ligament prosthesis such as described in European Patent Application 0238263, Swiss Patent 665,768 and corresponding European Patent Application 0201667. In this case, the implant has been employed as a cruciate ligament prosthesis and as described in the Swiss Patent have been formed of a plurality of concentric tubes of braided textile threads. In addition, the coreless braided tubes of the implant have been provided with zones of different flexibility and stretch. However, it has been found in practice with such implants, particularly in connection with the high-flexibility and high-stretch zones of the implant, that there is a risk of the discrete braided-together threads of the concentrically "superposed" tubes being abraded. This wearing due to rubbing leads to unwanted abraded particles in the body, particularly in the knee joint. In the course of time, these abraded particles weaken the mechanical strength of the implant.

Accordingly, it is an object of the invention to greatly reduce the abrasion of textile threads in an implant.

It is another object of the invention to prevent the egress of abraded material from a prosthetic implant into a body without change in the mechanical behavior of the implant.

It is another object of the invention to prevent abraded particles in a ligament prosthesis from egressing from the prosthesis into a surrounding body.

It is another object of the invention to prevent egress of abraded particles from a ligament prosthesis without changing the stressing. flexing and torsional properties of the prosthesis.

Briefly, the invention provides a prosthetic implant which is comprised of a plurality of concentrically disposed tubes wherein each tube is composed of textile threads. In accordance with the invention, a layer of elastomer is disposed over at least the outermost tube with the layer being impermeable to the passage of braided material from within the tubes and being of a thickness of at most 0.1 millimeters. In addition, the thickness of the elastomer between individual threads in the outermost tube is of a thickness of at most 0.1 millimeters.

The elastomer layer which surrounds at least the outermost tube and is impermeable to abraded material, the elastomer possibly being, with advantage, a polyurethane or a silicone, seals off the implant from its surroundings so that abraded material cannot issue from "inner" tubes into a joint. As a result of the resilience of the elastomer and of its reduced layer thickness, which can be determined, for example by light or electronic microscopy, the discrete threads of each impregnated tube can move relative to one another just like the threads which have not been impregnated with an elastomer, the resilience thereof ensuring that the cohesive material which is impermeable to abraded material is maintained at least in the outermost tube.

Not only the outermost tube but tubes which are disposed further inwards can of course be provided with a cohesive elastomer layer, for example, so as to obviate abraded material substantially completely. In this respect, at least some of the tubes are, with advantage, braided from threads impregnated with an elastomer. After preparation of the braiding, at least some of the already "elastomerized" filaments are joined together to form a cohesive layer impermeable to abraded material either by heat melting or by chemical dissolution.

Another advantageous way of producing the implant is first to prepare the implant, for example, by weaving or knitting or braiding, from elastomer-free threads which can be monofilament threads or consist of a large number of, for example, twisted together filaments, and then to impregnate the complete structure with an elastomer.

These and other objects and advantages of the invention will become more apparent from the following detailed description taken with the accompanying drawings wherein.

Figure 1:
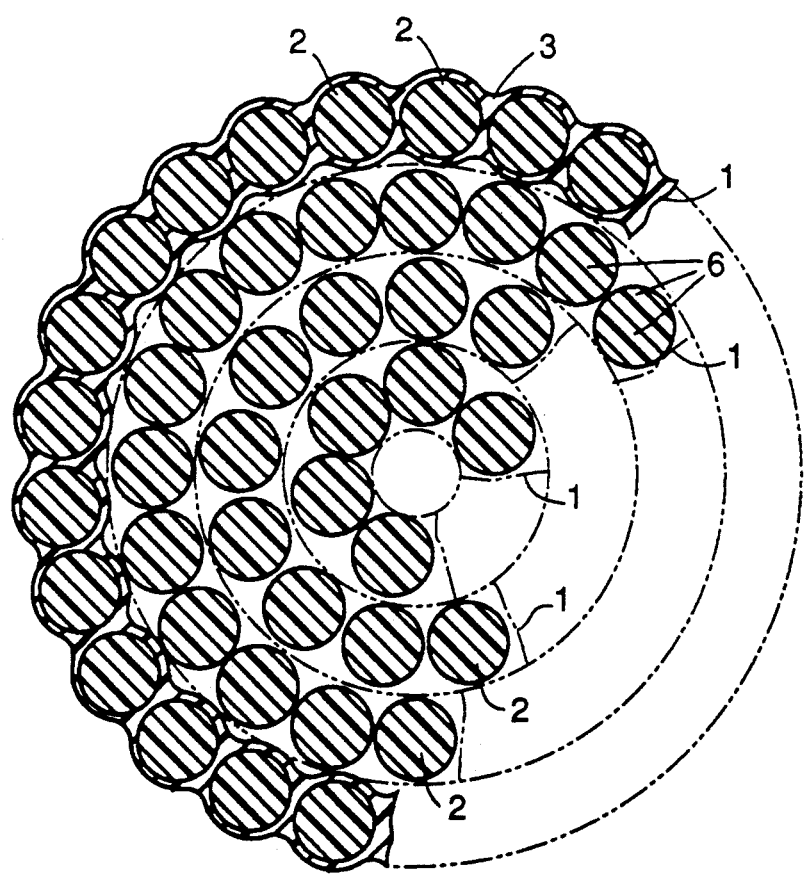
FIG. 1 illustrates a cross sectional view of a prosthetic implant constructed in accordance with the invention.

Referring to FIG. 1, the prosthetic implant comprises a plurality of concentrically disposed tubes 1 which extend around one another like the annual growth rings of a tree. The tubes 1 can be produced from monofilament or multifilament threads 2 and be made of natural fibers such as silk or cotton or of synthetic fibers such as polyester, polythene terephthalate. For a cruciate ligament prosthesis in a knee joint some 20 to 30 tubes 1 are layered one above another. In the present example, the discrete threads 2 each comprise a large number, for example, 40 to 60 filaments 6 which are twisted together and have a diameter, for example of from 0.01 to 0.30 millimeters (mm).

In the present case, the discrete tubes 1 are produced by braiding but they can be manufactured by other textile technologies such as weaving or knitting.

The discrete threads 2 of a tube 1 and of the tubes 1 together are joined together at least to some extent by "intermediate layers" of an elastomer 3 at least in the outer zones of the implant to form a layer which is impermeable to abraded material, the layer thickness of the elastomer 3 being at most 0.1 millimeters (mm). Consequently, there is little alteration in the mechanical behavior of the implant relative to that of an implant without elastomer 3.

Polyurethanes or silicones are preferred as elastomers 3.

The implant of FIG. 1 is first prepared from threads 2 not impregnated with elastomer 3, whereafter the implant is impregnated as a whole. Impregnation with the elastomer 3 can proceed, for example, as follows:

The braiding is first washed for a long time, for example, for 24 hours, in an aqueous solution of a cell-compatible commercially available detergent, then rinsed in repeatedly renewed water, then finally dried.

To increase the wettability of the threads 2 or of the filaments 6 the braiding is caused to swell in a dyeing accelerator (carrier). An accelerator of this kind is an organic solvent such as dichloromethane or tetrachloroethlene, dichlorobenzene or trichlorobenzene.

The swollen braiding is then dipped into a polyurethane (PUR) solution in which dimethyl formamide is the solvent and which impregnates the braided structure. After impregnation, the structure is dried by an air flow in a laminar flow chamber.

To remove solvent residues, the implant is finally vacuum treated at 50° C. and approximately 1 millimeters (mm) HG, the implant previously having been packed in a vapor-pervious foil.

Figure 2:
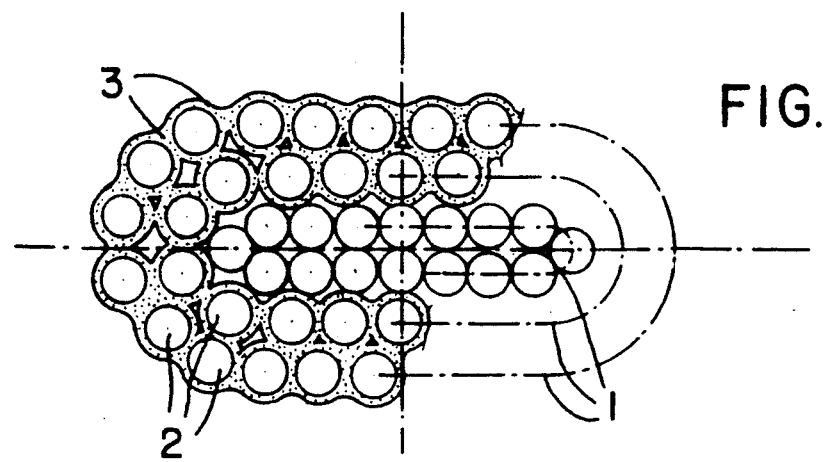
FIG. 2 illustrates a modified implant having concentric tubes flattened to a general oval cross-section in accordance with the invention.

Referring to FIG. 2, wherein like reference characters indicates like parts as above, the braiding of at least the outer tube or tubes 1 is prepared from threads 2 which have already been impregnated with an elastomer 3. Such threads 2, which are made, for example, of polyester and which have been impregnated with polyurethane, are commercially available. To produce, at least in the outermost tube 1, a cohesive elastomer layer not permeable to abraded material, the elastomer 3 of the finished braiding is partly dissolved by a solvent, whereafter the solvent is expelled.

Alternatively, if a relatively high-melting-point material is used for the threads 2 and a low-melting-point elastomer 3 is used, the braiding can be heated to the melting range of the elastomer 3 so that the elastomer melts at least on the outer surface, flows mergingly from the discrete threads and solidifies on cooling to form a closed layer.

In this case, either, as in the foregoing, threads 2 which consist of a single material and which have been treated with elastomer 3 can be used or multifilament threads 2 consisting mainly of a high-melting-point material, for example, polythene terephthalate, and additional filaments of a lower-melting-point elastomer material, such as, for example, polythene, can be used.

Figure 3:
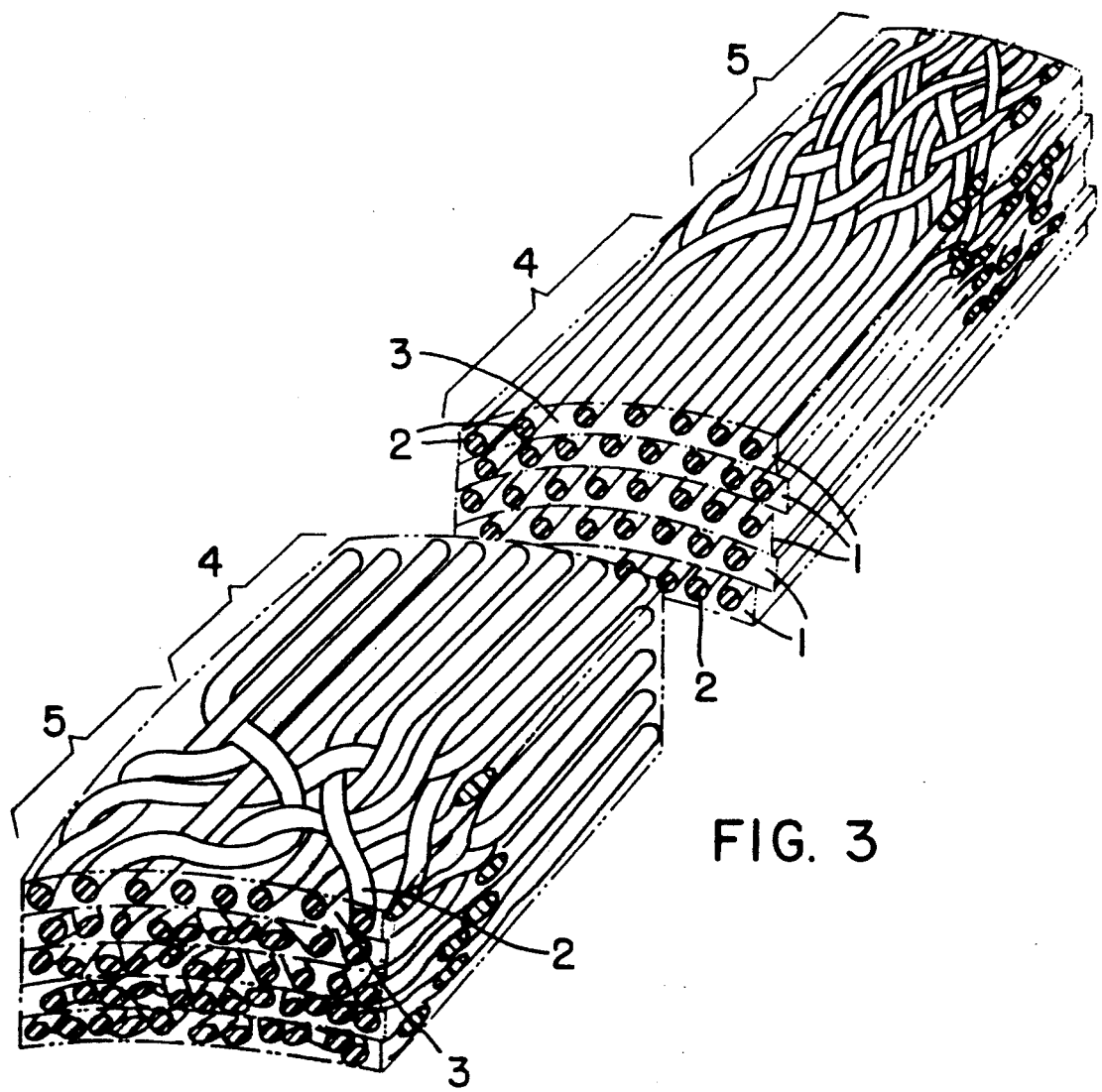
FIG. 3 illustrates an outcut of an implant similar to that shown in FIG. 2 wherein the implant includes zones of different flexibility and stretch.

As shown in FIG. 3, the tubes 1 may be constructed to have zones 4 and 5, each zone having different flexibility and stretch throughout the length of the implant. In such cases, at least the zones 5 of high-stretch in the outermost tube would have the elastomer 3 therein.

The invention thus provides a prosthetic implant in which the abrasion of textile threads can be greatly reduced within the implant while at the same time the egress of abraded material from the implant into the body can be prevented. Furthermore, these advantages can be obtained without any change in mechanical behavior of the implant particularly with respect to the stretching, flexing and torsional properties of the implant.

What is claimed is:

1. A prosthetic implant comprising
   a plurality of concentrically disposed braided tubes, each said tube being composed of textile threads; and
   a layer of elastomer disposed over at least an outermost tube, said layer being impermeable to the passage of abraded material from within said tubes and being of a thickness of at most 0.1 millimeters, wherein each braided tube consists of multi-filament threads, of first portion of said individual filaments being composed of a first material and a second portion of said individual filaments being composed of a second material, wherein said first material has a higher melting point than said second material.

2. An implant as set forth in claim 1 wherein said threads contain filaments of polythene terephthalate and polythene.

* * * * *

UNITED STATES PATENT AND TRADEMARK OFFICE
CERTIFICATE OF CORRECTION

PATENT NO. : 5,176,708
DATED : January 5, 1993
INVENTOR(S) : Frey et al.

It is certified that error appears in the above-indentified patent and that said Letters Patent is hereby corrected as shown below:

```
Column 2, line 35, change "polythene" to --polyethylene--;
Column 2, line 65, change "dyeing" to --drying--;
Column 2, line 68, change "chloroethlene" to --chloroethylene--;
Column 3, line 26, change "threads" to --threads 2--;
Column 3, line 32, change "polythene" to --polyethylene--;
Column 3, line 34, change "polythene" to --polyethylene--;
Column 4, line 25, change "of first" to --a first--;
Column 4, line 32, change "polythene" to --polethylene--;
Column 4, line 33, change "polythene" to --polyethylene--;
```

Signed and Sealed this

Sixth Day of December, 1994

Attest:

BRUCE LEHMAN

Attesting Officer

Commissioner of Patents and Trademarks